United States Patent [19]

Häyry et al.

[11] Patent Number: 6,124,256
[45] Date of Patent: Sep. 26, 2000

[54] METHOD FOR THE PREVENTION OF A PATIENT'S FIBROPROLIFERATIVE VASCULOPATHY

[76] Inventors: Pekka Häyry, Sakkolan kylatie 292, FIN-09120 Karjalohja, Finland; Yogesh C. Patel, 655 Roslyn Ave., Westmount, Quebec, Canada, H3Y 2V1

[21] Appl. No.: 09/049,020

[22] Filed: Mar. 27, 1998

[51] Int. Cl.[7] ................................................. A61K 38/00
[52] U.S. Cl. ................................ 514/2; 514/12; 514/13; 514/14; 530/311
[58] Field of Search ........................ 514/2, 12, 13, 514/14; 530/311

[56] References Cited

FOREIGN PATENT DOCUMENTS

WO 97/14715   4/1997   WIPO .
9743278   11/1997   WIPO .

OTHER PUBLICATIONS

Wahlers et al., *The Journal of Heart and Lung Transp.*, vol. 14, No. 1, Part 1, 143–150, 1995.
Hcaplus on 128: 136659, Zhao et al., *Prustaglandins*, 54(5), 781–793 (abstract), 1997.
Hcaplus on 125: 185985, Mutumura et al., *Transplant Immunol.*, 4(2), 99–104, 1996.
WPIDS Doc. No. CPI: C98–013891, WO 9743278, 1997.
Hcaplus on 120:125371, Howell et al., *Clin. Sci* 85(2), 183–188, 1993.
Eriksen et al., "Randomized Double–blind Scandinavian trial . . . ," *American Heart J.* 130(1):1–8 (1995) (Abstract).
Emanuelsson et al., "Coronary Heart Disease/Myocardial . . . ," *Circulation* 91(6):1689–1696 (1995).
von Essen et al., "Effects of Octreotide Treatment . . . ," *Circulation* 96(5):1482–1487 (1997).
Foegh et al., "Early Inhibition of Myointimal Proliferation . . . ," *J. Vasc. Surg.*, 19(6):1084–1091 (1994) (Abstract).
Foegh et al., "Angiopeptin: Experimental and Clinical Studies . . . ," *Kidney Int.—Supp*, 52:S18–22 (1995) (Abstract).
Galis et al., "Enhanced Expression of Vascular Matrix . . . ," *Ann. NY Acad. Sci.*, 748:501–507 (1995) (Abstract).
Goldberg et al., "Vascular Smooth Muscle Cell Kinetics . . . ," *Science* 205 (4409):920–922 (1979) (Abstract).
Grant et al., "Localization of Insulin–like Growth Factor . . . ," *Circulation* 89 (4):1511–1517 (1994).
Yumi et al., "Direct Effects of Somatostatin Analog . . . ," *Lab. Invest.* 76 (3):329–338 (1997) (Abstract).
Häyry et al., "Somatostatin Analog Lanreotide Inhibits . . . ," *FASEB J.*, 7:1055–1060 (1993).
Khare et al., "Differential Regulation of Somatostatin Receptor Types 1–5 in Rat Aorta After Angioplasty," 13 *FASB J.* 387–394 (Feb. 1999).
Weckbecker et al., "The Somatostatin Analog Octreotide as Potential Treatment for Re–Stenosis . . ," 29 *Transplantation Proc.* 2599–2600 (1997).
Chen et al., "Somatostatin Receptor Expression in Rat Iliac Arteries After Balloon Injury," 10 *J. Investigative Surg.* 17–23 (1997).
Patel, "Molecular Pharmacology of Somatostatin Receptor Subtypes," 20 *J. Endocrinol. Invest.* 348–367 (1997).

*Primary Examiner*—Dwayne C. Jones
*Assistant Examiner*—C. Delacroix-Muirheid
*Attorney, Agent, or Firm*—James C. Lydon

[57] ABSTRACT

A method for the prevention of a patient's fibroproliferative vasculopathy following vascular injury or a vascular surgical operation. The method includes administering to the patient an agonist specific for at least one somatostatin (SST) receptor showing an increased expression in the patient's vascular wall subsequent to injury or operation, the administering being carried out for one to two weeks after the injury or surgical operation.

10 Claims, 4 Drawing Sheets

(2 of 4 Drawing Sheet(s) Filed in Color)

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: other nucleic acid
      (A) DESCRIPTION: /desc = "primer"

(xi) SEQUENCE DESCRIPTION: SEQ ID NO:1:

ATGTTCCCCA ATGGCACC                                          18

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iv) ANTI-SENSE: YES (xi) SEQUENCE DESCRIPTION: SEQ ID NO:2:

CAGATTCTCA GGCTGGAAGT CCTC                                               24

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:3:

AGCAACGCGG TCCTCACGTT                                                    20

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iv) ANTI-SENSE: YES (xi) SEQUENCE DESCRIPTION: SEQ ID NO:4:

GGAGGTCTCC ATTGAGGAGG                                                    20

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:5:

ATGAGCACGT GCCACATGCA G                                                  21

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iv) ANTI-SENSE: YES

-continued (xi) SEQUENCE DESCRIPTION: SEQ ID NO:6:

ACAGATGGCT CAGCGTGCTG                                              20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:7:

ATGGTAACTA TCCAGTGCAT                                              20

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iv) ANTI-SENSE: YES (xi) SEQUENCE DESCRIPTION: SEQ ID NO:8:

GTGAGGCAGA AGACACTCGT GAACAT                                       26

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

TGGTCACTGG TGGGCTCAGC                                              20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(iv) ANTI-SENSE: YES (xi) SEQUENCE DESCRIPTION: SEQ ID NO:10:

CCTGCTGGTC TGCATGAGCC                                              20

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single -continued

```
        (D) TOPOLOGY: linear (ii) MOLECULE TYPE: other nucleic acid
         (A) DESCRIPTION: /desc = "primer"

(xi) SEQUENCE DESCRIPTION: SEQ ID NO:11:

ATCATGAAGT GTGACGTGGA C                                              21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
         (A) DESCRIPTION: /desc = "primer"

(iv) ANTI-SENSE: YES (xi) SEQUENCE DESCRIPTION: SEQ ID NO:12:

AACCGACTGC TGTCACCTTC A                                              21
```

METHOD FOR THE PREVENTION OF A PATIENT'S FIBROPROLIFERATIVE VASCULOPATHY

FIELD OF THE INVENTION

This invention relates to a method for the treatment of prevention of a patient's fibroproliferative vasculopathy such as chronic allograft rejection or vascular restenosis following vascular trauma.

BACKGROUND OF THE INVENTION

The publications and other materials used herein to illuminate the background of the invention, and in particular, cases to provide additional details representing the practice, are incorporated by reference.

Fibroproliferative vasculopathy includes restenosis following coronary bypass surgery and PTCA (percutaneous transluminal coronary angioplasty), allograft arteriosclerosis in chronic allograft rejection, diabetic angiopathy and all forms of common arteriosclerosis.

Vascular intimal dysplasia and remodelling are characteristic features of reinjury following balloon angioplasty, coronary bypass surgery (Holmes et al. 1984; Holmes et al. 1988) and in chronic allograft rejection (Lemström and Koskinen, 1997; Häyry et al. 1993). The initial response to vascular injury is inflammatory and involves attraction of lymphocytes, macrophages and thrombocytes to the site of injury and secretion of cytokines, eicosanoids and growth factors (Ross 1993). Under the influence of growth factors and cytokines, smooth muscle cells (SMC) proliferate and migrate from the media to the intima and contribute to intimal hyperplasia and stenosis. The key mediators of SMC proliferation and migration are IL-1, TNFα, PDGF, IGF1, bFGF, EGF, TGFβ and VEGF (Asahara et al. 1995; Bornfeldt et al. 1994; Ferns et al. 1991; Libby and Galis 1995, Galis et al. 1995; Gronwald et al. 1989; Hancock et al. 1994; Häyry et al. 1995; Lindner and Reidny 1991; Myllärnemi et al. 1997; Nabel et al. 1993; Shi et al. 1996; Tanaka et al. 1996) and the matrix metalloproteinases in SMC locomotion through the extracellular matrix (Bendeck et al. 1996; Galis et al. 1995). In view of the central role of SMC proliferation, therapeutic strategies designed to prevent stenosis have attempted to suppress SMC proliferation by blocking the production and action of growth factors and cytokines with receptor antagonists or antisense oligonucleotides directed against cell cycle regulatory molecules (Häyry et al. 1995; Myllärniemi et al. 1997; Sirois et al. 1997; Wrighton et al. 1996). One important inhibitor of mitogenic signalling is somatostatin (SST) (Grant et al. 1994; Hong et al. 1993; Yumi et al. 1997).

The neurohormone SST is produced widely in the body and acts both systemically via the circulation and locally to inhibit cell proliferation as well as the secretion of various hormones, growth factors and neurotransmitter substances, SST and its metabolically more stable synthetic analogs, such as SMS201-995 (octreotide) and BIM23014 (lanreotide, angiopeptin), exert a number of vascular effects such as vasoconstriction in the gut and inhibition of angiogenesis. The actions of SST are mediated by a family of five heptahelical G protein coupled receptors termed SSTR1–5. All five SSTRs are functionally coupled to inhibition of adenylyl cyclase. Some of the receptor isotypes also modulate other effectors such as phosphotyrosine phosphatase, $K^-$ and voltage-dependent $Ca^{2+}$ ion channels, a $Na^+/H^+$ exchanger, phospholipase $A_2$ and MAP kinase (MAPK).

Based on structural similarity and the ability to react with octapeptide and hexapeptide SST analogs, the SST receptor family can be subdivided into two categories: the SSTR2,3,5 category with high affinity to these analogs and the SSTR1,4 category with low affinity to these compounds (see Table).

In experiments using arterial, venous, and vascular transplant models in various animal species, the administration of octreotide or lanreotide prevents the formation of dysplastic lesions (Foegh et al. 1994; Foegh and Ramwell 1995; Grant et al. 1994; Hong et al. 1993; Yumi et al. 1997; Häyry et al. 1993). These results however, have been inconsistent in different experimental models. In randomized placebo controlled clinical traits, lanreotide in some studies has been shown to prevent restenosis after percutaneous transluminal angioplasty as quantitated by angiography or as clinical events (Eriksen et al. 1995; Emanuelsson et al. 1995), whereas the same therapeutic response has not been achieved with octreotide (von Essen et al. 1997). Differences in the binding specificity of the SST analogs for the five SSTRs as well as the dose and duration of administration of SST analogs may contribute in part to the inconsistent results obtained in these studies. For instance, octreotide and lanreotide both bind with high affinity to SSTR2 and SSTR5 but display species-dependent-variability in binding to SSTR3; octreotide binds well to human SSTR3 but shows only moderate affinity for the rodent receptor, whereas the opposite is the case for lanreotide. To optimize the vasculoprotective effect of SST, the ideal approach would be to characterize the pattern of expression of SSTRs in the vascular wall after trauma, and to target the subtypes involved with appropiate agonists. Towards this objective, we have determined the time course of expression of mRNA for SSTR1–5 in rat aorta after endothelial denudation (balloon injury) by reverse transcription polymerase chain reaction (RT-PCR) and localized the reseptors directly by immunocytochemistry with rabbit polyclonal antibodies to receptor subtype specific peptides.

OBJECT AND SUMMARY OF THE INVENTION

The object of this invention is thus to characterize level of expression of somatostatin receptors (SSTRs) versus time in the intimal layer of the vascular wall after trauma (vascular injury or vascular surgery), and to target the receptor subtypes showing increased expression after trauma, with appropriate agonists so as to avoid fibroproliferative vasculopathy of the patient's blood vessels which have been subjected to trauma.

The invention thus concerns a method for the prevention of a patient's fibroproliferative vasculopathy following vascular injury or a vascular surgical operation, said method comprising the administering to said patient an agonist specific for at least one somatostatin (SST) receptor showing an increased expression in the patient's vascular wall subsequent to injury or operation, said administering being carried out for one to two weeks after the injury or surgical operation.

BRIEF DESCRIPTION OF THE DRAWINGS

The file of this patent contains at least one microphotograph executed in color. Copies of this patent with color microphotograph(s) will be provided by the Patent and Trademark Office upon request and payment of the necessary fee.

DETAILED DESCRIPTION OF THE INVENTION

Figure 1:
FIG. 1 shows Southern blots of mRNA RT-PCR products for the five SSTR subtypes at different times in control and in denuded aortic samples.

The experiments carried out and discussed below were performed in rat. The expression of the individual subtypes of the SST receptors are, however, believed to follow the same pattern in other mammals, including man.

According to a preferred embodiment, an SST receptor subtype which is present in the intimal layer of the vascular wall and shows an increased expression during the first week following the injury or the surgical operation should be activated by the agonist. The process of wound healing is essentially completed after two weeks. A prolonged activation of an highly expressed SST receptor after this point would not have any restenosis preventing action.

According to a preferred embodiment, the SSTR1 or SSTR4 receptor should be activated.

According to a preferred embodiment, the SST receptor active agonist is a compound such as somatostatin SRIF-14, somatostatin SRIF-28 or DADI-SST14(desAA$^{1,2,5}$[D-Trp$^6$-N-p-isopropyl-4-aminomethyl-L-phenylalanine]-SST14). The structure and binding affinities of somatostatin and its analogues mentioned above have been disclosed in Patel YC (1997).

The table below shows a comparison of binding affinities $K_i$ (nM) somatostatin and its key cyclic analogs Ianreotide and octeoride and DADI-SST14 for five human somatostatin receptors in transfected CHO cell lines. The data are provided by PC Patel.

| Ligand | hSSTR1 | hSSTR2 | hSSTR3 | hSSTR4 | hSTR5 |
| --- | --- | --- | --- | --- | --- |
| Somatostatin (SRIF-28) | 2.2 | 4.1 | 6.1 | 1.1 | 0.07 |
| Somatostatin (SRIF-14) | 1.1 | 1.3 | 1.6 | 0.53 | 0.9 |
| DADI-SST14 | 3.2 | >1000 | >1000 | 4.3 | >1000 |
| Lanreotide | >1000 | 1.8 | 43 | 66 | 0.62 |
| Octeoride | >1000 | 2.1 | 4.4 | >1000 | 5.6 |

According to a preferable embodiment, the selected SST-receptor is the SST-receptor subtype 1 or subtype 4 and the agonist is somatostatin SRIF-14.

The method according to this invention is useful in the prevention of the patient's fibroproliferative vasculopathy following vascular trauma.

According to one embodiment, the method according to this invention is useful to prevent vascular restenosis following balloon angioplasty or a coronary bypass operation. However, the invention is not restricted hereto. The pattern of expression for the various SST receptor subtypes found in the aorta is believed to exist throughout the patient's vascular system. The invention is therefore applicable to the prevention of restenosis following any vascular trauma in the patient's body.

According to another embodiment, the method according to this invention is useful for the prevention of a patient's chronic allograft rejection.

The term "SST receptor active agonist" shall be understood to include the compound as such as well as any pharmaceutically acceptable derivative thereof such as salt, ester etc.

For the purpose of the invention, the SST receptor active agonist can be administered by various routes but preferable by systemic routes. The suitable administration forms include, for example, oral formulations, parenteral injections including intravenous, intramuscular, intradermal and subcutaneous injections; or transdermal administration forms.

The required dosage of the compounds of the SST receptor agonist will vary with the particular condition being treated, the severity of the condition, the duration of the treatment, the administration route and the specific compound being employed. The therapeutically effective dose for a particular compound can, for example, be in the range 1–10 μg per kg of body weight and day. The suitable period of treatment is one to two weeks after the trauma, preferably two weeks. If the trauma is caused by surgical operation, the administration of the agent is preferable started one day before the surgical operation.

The invention is demonstrated by the following experiments.

MATERIALS AND METHODS

Aortic Denudations

Male Wistar rats weighing 200–300 g were anesthetized with chloral hydrate (240 mg/kg i.p.). The thoracic aorta was denuded of endothelium using a 2F Fogarty arterial embolectomy catheter (Baxter Healthcare Corporation, Santa Ann, Calif.). The catheter was introduced into the thoracic aorta via the left iliac artery, inflated with 0.2 ml air, and passed five times to remove the endothelium. The iliac artery was ligated and the animals allowed to recover (Clowes et al. 1983; Haudenschild and Swartz 1979). Buprenorphine (Temgesic, Reckitt Colman, Hull, England) was administered for peri- and posoperative pain relief. Groups of 3–5 rats were sacrificed at 15 min, 3 days, 7 days, 14 days and 60 days and aortic tissue removed for evaluation of SSTR expression. All animals received humane care in compliance with the Principles of Laboratory Animal Care and the Guide for the Care and Use of Laboratory Animal prepared and formulated by the National Institute of Health (NIH Publication No. 86-23, revised 1985).

Three separate experiments were performed. In the first experiment, 12 rats were denuded and 15 coded speciments of thoracic vascular tissue (3 control , 12 denuded; 3 specimens/time point) were collected for RNA isolation and RT-PCR. In the second experiment, 20 rats were denuded and 25 coded speciments were collected for RNA isolation and RT-PCR (5 specimen/time point). Four of these were used for RNA isolation and RT-PCR and the fifth specimen for routine histology, quantitation of cell replication, and SSTR immunocytochemistry. In the third experiment, frozen sections of 20 aortas (4 control, 16 denuded) were processed for immunocytochemistry for SSTR1–5. The results described here derive from experiments 2 and 3.

For RNA isolation, aortic tissue specimens were flash frozen in liquid nitrogen and stored at −80° C. for RNA isolation. For evalution of morphological changes, aortic cross sections from the mid segment of the denuded area were fixed in 3% paraformalhyde (pH 7.4), embedded in paraffin for sectioning and stained with Mayer's haematoxylin and eosin (HE). For immunocytochemistry, aortic specimens were embedded in Tissue-Tek (Miles Inc. Elkhard, Ind.) and snap frozen in liquid nitrogen. Serial frozen sections (4–6 μm) were air dried on silane coated slide, fixed in acetone at −20° C. for 20 min and stored at −20° C. until used.

Reverse Transcription Polymerase Chain Reaction (RT-PCR)

Weighed vascular tissue samples were pulverized in liquid nitrogen using a mortar and pestle and total RNA isolated using the standard technique of quanidinium isothiocyanate-phenol-chloroform extraction. For reverse transcription, 20 μg total RNA was treated with 10 units/mg RQ1 Rnase-free Dnase1 (Promega) in 40 mM Tris buffered HCl, pH 7.9, 10 mM NaCl, 6 mM $MgCl_2$, 10 mM $CaCl_2$ for 30 min at 37° C. The DNase1 was inactivated by phenol chloroform extraction followed by ethanol precipitation. Five μg of DNA-free RNA was then incubated in 20 μl reaction containing 20 mM Tris-HCl, pH 8.4, 50 mM KCl, 5 mM $MgCl_2$, 1 mM dNTPs, 20 units of RNasin (Promega), 100 pmol of random hexanucleotides (Pharmacia), 200 units of Moloney murine leukemia virus (MMLV), reverse transcriptase (Gibco BRL) at 42° C. for 30 min. Four μl of the resulting cDNA samples were denatured at 94° C. in 20 mM Tris HCl, pH 8.4, 50 mM KCl, 1.5 mM $MgCl_2$, 200 mM dNTPs, and 20 pmol each of SST1–5 primers in 50 μl reaction volume for 10 min. The following primers were used for the PCR amplification:

hybridization bands were quantitated in the linear range, each blot was exposed to x-ray film for several different times. Only bands that did not reach saturation density of exposure were subjected to quantitative analysis. The units derived from the Java analysis were arbitrarily assigned a pixel density corrected for background. Values of SSTR1–5 mRNA expression were normalized to those of actin mRNA on the same gels. All experiments were performed at least 3 times and each mRNA quantitation represents the average of six measurements.

BrdU Staining of Proliferating Cells

The method used was modified from the radioisotope method of Goldberg et al. 1979. Cell proliferation was quantitated by Bromodeuxyuridine labelling (BrdU-Zymed Laboratories, San Francisco, Calif.) according to the manufacturer's instructions. Rats were injected with 0.3 ml BrdU labelling reagent for 4 h before sacrifice and cellular incorporation was visualized by staining of paraffin cross sections using a mouse primary antibody (Bu20a, Dako A/S, Denmark) and Vectastain Elite ABC Kit (Vector Laboratories, Burlingame, Calif.). Sections were deparaffinized and microwave-treated at 500 W for 2×5 min in 0.1 M citrate buffer, pH 6, followed by treatment in 95% formamide in 0.15 M tri-sodium citrate at 70° C. for 45 min. Antibody dilutions were made according to the manufacturer's instructions. Sections were counterstained with Mayers

```
rSSTR1:  Sense:     5' ATGTTCCCCAATGGCACC 3' (nt 1-18)              (SEQ ID NO:1)
         Antisense: 5' CAGATTCTCAGGCTGGAAGTCCTC 3'(nt 1093-1115)     (SEQ ID NO:2)

rSSTR2:  Sense:     5'AGCAACGCGGTCCTCACGTT 3' (NT 124-143)           (SEQ ID NO:3)
         Antisense: 5' GGAGGTCTCCATTGAGGAGG 3' (nt 1077-1196)        (SEQ ID NO:4)

rSSTR3:  Sense:     5' ATGAGCACGTGCCACATGCAG 3'(nt 565-585)          (SEQ ID NO:5)
         Antisense: 5' ACAGATGGCTCAGCGTGCTG 3'(nt 1266-1286)         (SEQ ID NO:6)

rSSTR4:  Sense:     5' ATGGTAACTATCCAGTGCAT 3'(nt 127-147)           (SEQ ID NO:7)
         Antisense: 5' GTGAGGCAGAAGACACTCGTGAACAT 3'(nt 376-401)     (SEQ ID NO:8)

rSSTR5:  Sense:     5' TGGTCACTGGTGGGCTCAGC 3'(nt 70-89)             (SEQ ID NO:9)
         Antisense: 5' CCTGCTGGTCTGCATGAGCC 3'(nt 1067-1086)         (SEQ ID NO:10)

β-actin: Sense:     5' ATCATGAAGTGTGACGTGGAC 3'(nt 90-110)           (SEQ ID NO:11)
         Antisense: 5' AACCGACTGCTGTCACCTTCA 3'(nt 529-549)          (SEQ ID NO:12)
```

PCR reaction was initiated by the addition of 2.5 units of Taq polymerase (Gibco BRL) at 85° C. (hot start). The following conditions were used: SSTR1,2,4-denaturation at 94° C. for 1 min annealing at 55° C. for 30 seconds and extension at 72° C. for 90 second; SSTR3,5-denaturation at 94° C. for 1 min, annealing at 64° C. for 30 seconds and extension at 72° C. for 90 seconds. The receptors were coamplified with β-actin for 30 cycles followed by final extension at 72° C. for 10 min.

Southern Transfer and Hybridization

10 μl PCR products were separated by electrophoresis on 1.2% agarose gels, transferred to Genescreen Plus Membranes (Dupont), and hybridized with $^{32}P$ labelled SSTR1–5, and β-actin-specific cDNA probes labelled to high specific activity by random hexanucleotide primers using a Life Technologies Kit. Following hybridization for 20–22 h at 70° C., filters were washed and exposed to Kodak XAR film at four different times. The hybridization signals were quantitated using a Java Video Analysis Software Package (Jandel Scientific, Corte Madera, Calif.) and used as an index of SST and actin mRNA. To ensure that the haematoxylin and eosin and positive cells in intimal, medial, and adventitial layers were separately counted and analysed.

Antibodies to SSTR1–5 and Immunohistochemistry of SSTR1–5 Antigens

Antipeptide rabbit polyclonal antibodies specific to SSTR1–5 were produced and characterized as previously described. Synthetic oligopeptides corresponding to deduced sequences in the amino terminal segment or extracellular loop 3 of hSSTR1–5 were conjugated to keyhole limpet hemocyanin and used to immunize New Zealand white rabbits. The sequences selected were identical or nearly identical between the human and rat SSTR isoforms. Anti-SSTR activity in rabbit sera was screened by the ability to inhibit $[^{125}I$-LTT]SST-28 binding to membrane SSTRs, by immunocytochemistry of stable CHO-K1 cells individually transfected with hSSTR1–5 and by Western blot analysis (SSTR2). Before immunostaining, the slides were refixed with chloroform and dried in air as described by Lemström and Koskinen 1997. After incubation with 1.5% normal goat serum, frozen sections were incubated with the panel of SSTR1–5 primary antibodies (diluted 1:200 to 1:500) at 4° for 12 h. With intervening washes in Tris buffered saline, the sections were incubated with goat antirabbit rat absorbed secondary antibody at room temperature for 30 min followed by exposure to avidin-biotinylated horseradish peroxidase complex (Vectastatin Elite, ABC Kit) in phosphate buffered saline at room temperature for 30 min. The reaction was revealed by chromogen 3-amino-9-ethylcarbazole (AEC Sigma) containing 0.1% hydrogen peroxide, yielding a brown-red reaction product. Specimens were counterstained with hematoxylin and coverslips were mounted (Aquamount BDH Ltd.). The controls used to validate the specificity of the SSTR immunoreactivity included preimmune serum in place of primary antibody and primary antibody absorbed with excess antigen.

Statistical Analysis

Statistical significance at different time points after vessel injury was determined by analysis of variance followed by the Bonferron t-test. P values <0.05 were considered statistically significant.

RESULTS

Vascular Cell Proliferation in Response to Denudation Injury

To validate the model against previous reports (Clowes et al. 1983; Haudenschild and Swartz 1979; Häyry et al. 1995) we tested the proliferative and intimal response of denuded aorta at the time points selected for the determination of SSTR and mRNA and protein levels. Following denudation, the endothelial lining was completely removed. Quiescent cells in the media were induced to proliferation beginning on day 3 followed by migration and further proliferation in the intima on day 7–14. Staining with antibody to α-SMC actin and α-leukocyte common antigen (α-LCA) demonstrated that virtually all cells in the media and >95% of cells in the intima expressed α-actin and <5% of the intimal cells were positive for α-LCA indicating that they were muscle cells (not shown).

Expression of SSTR1–5 mRNA in the Vascular Wall After Trauma

Figure 2:
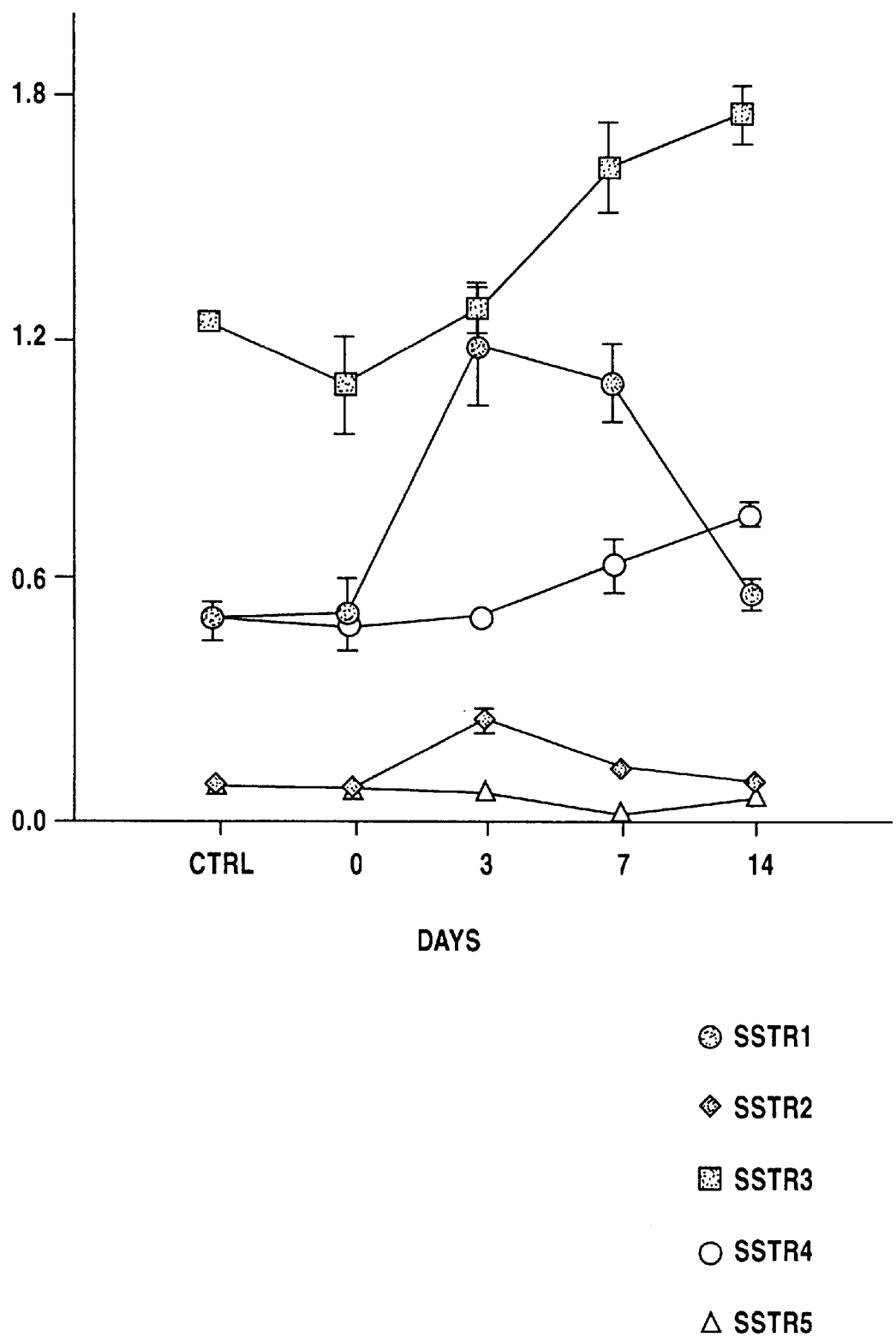
FIG. 2 shows the mean expression level versus time for mRNA of five SSTR subtypes following vascular injury.

FIG. 1 depicts Southern blots of RT-PCR products showing the expression of the quadruple specimens of mRNA for the five SSTR subtypes at different times in control and denuded aortic samples. The time course of the mean levels of expression of expression of mRNA for the five SSTR subtypes following vascular injury is summarized in FIG. 2. Control aorta expressed readily detectable levels of SSTR3 mRNA, moderate levels of SSTR1 and SSTR4 mRNA, and barely detectable concentrations of SSTR2 and SSTR5 mRNA. Following injury, SSTR1 mRNA displayed a dramatic 2-fold increase at day 3 ($p<0.01$) concomitantly with the SMC proliferation in the media and intima. The mRNA level remained elevated at day 7 ($p<0.01$), concomitantly with SMC proliferation in the intima, but declined thereafter to baseline concentration by day 14 when the proliferation was over. A parallel increase in SSTR2 mRNA was also observed at day 3 ($p<0.01$) although the magnitude of the change (~20%) was considerably smaller than that of SSTR1 mRNA. Unlike SSTR1 and SSTR2, SSTR3 mRNA showed a more gradual increase with no change at day 3 followed by a significant increase by 30% at day 7 ($p<0.01$) and by 40% at day 14 ($p<0.001$). SSTR4 mRNA followed a similar pattern but the magnitude of the increase was smaller (20%) and statistically significant ($p<0.05$) at day 7 and ($p<0.001$) at day 14. In contrast to the other 4 subtypes, SSTR5 mRNA remained virtually undetectable and its expression pattern did not change following injury.

Expression of hSSTR1–5 by Immunohistochemistry

Figure 3A:
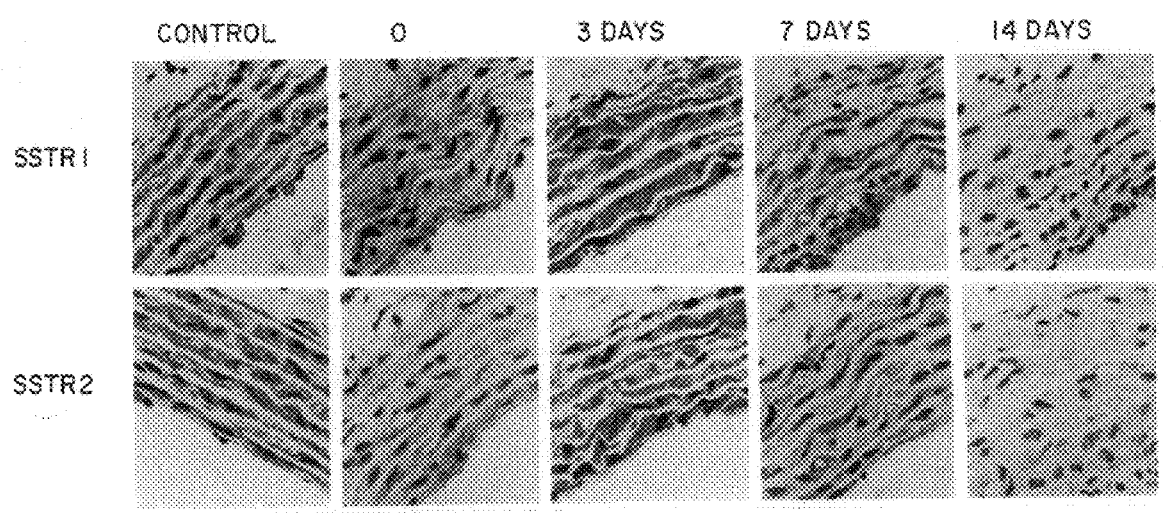
FIG. 3A is a set of color microphotographs which show the immunoreactivity of the SSTR1 and SSTR2 subtypes at different times in control and in denuded aortic samples.
Figure 3B:
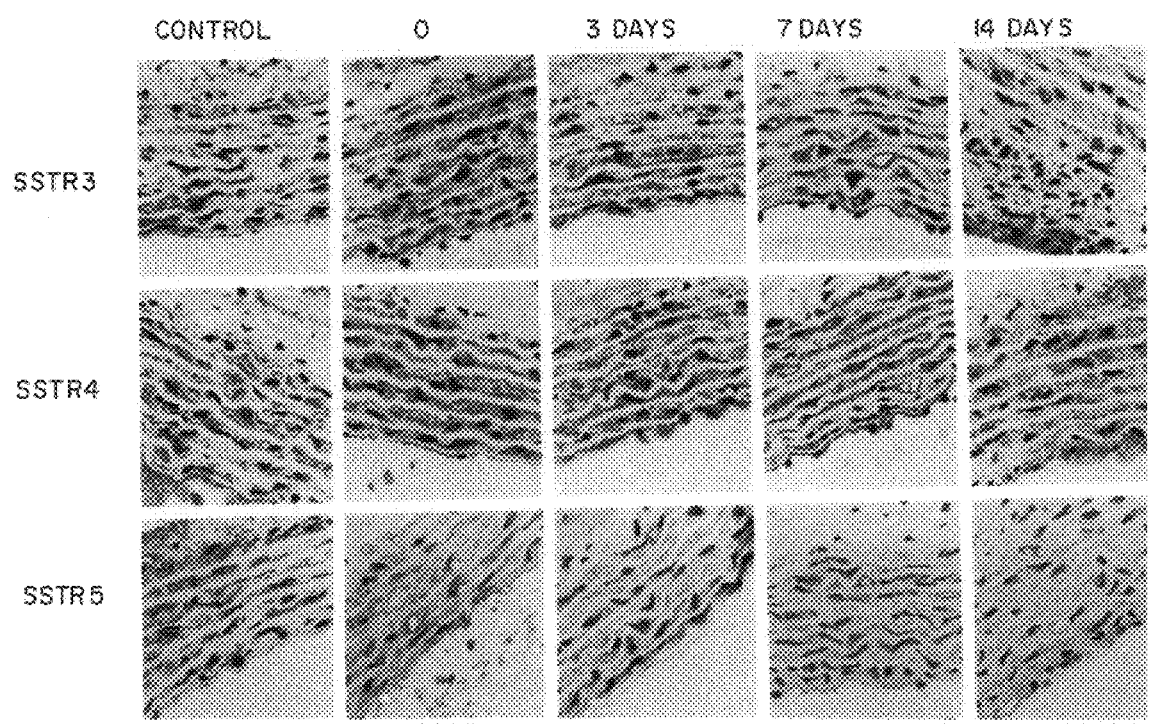
FIG. 3B is a set of color microphotographs which show the immunoreactivity of the SSTR3, SSTR4 and SSTR5 subtypes at different times in control and in denuded aortic samples.

FIGS. 3A and 3B depict the expression and localization of the five SSTR subtype reactor proteins in injured vessel wall after denudation injury, as detected by subtype specific rabbit antisera and immunoperoxidase staining. In all microphotographs, lumen is facing down and adventitia is facing up, as exemplified in the microphotograph in the left upper corner. It should be noted that all immunoreactivity is observed in the media and intima and none in the adventitia, and that the cells in the intima display mostly SSTR subtypes 1 and 4.

The results largely confirm the RNA expression analysis. The SSTR1,2,4 subtypes were expressed at a low levels in the media of the non-denuded (control) aorta, but very little if any of SSTR3 and SSTR5 was seen. After denudation, SSTR1 was expressed in the media on day 3, when media proliferation occurred, and strongly in the intima on day 7 and 14 at the time of proliferation in the intima. The expression of SSTR4 subtype was faint in the media on days 3 and 7, but increased in the intima on days 14 and 60 and correlated with increased intimal thickening. SSTR3 was recorded faintly in the media and intima until day 60, when it was expressed in the innermost layer (luminal side) of the intima. SSTR2 and SSTR5 were seen in the intima only faintly if at all.

DISCUSSION

The model used in this study for the quantitation of SMC replication and migration after endothlial injury of rat aorta has been well established in the past (Goldberg et al. 1979; Clowes et al. 1983; Clowes et al. 1983). Needless to say, the injury in this model is performed in healthy vessel and not to a vessel with atheromatous changes, as for example coronary balloon dilation in man is performed. Nevertheless the model can be used to investigate smooth muscle cell migratory and proliferative responses. The model has previously been extensively characterized by a number of investigators (Clowes et al. 1983; Clowes and Swartz 1985; Häyry et al. 1995; Majesky et al. 1990; Majesky et al. 1992) demonstrating that after injury the medial cells begin to proliferate on day 2, reach the proliferation peak on day 3 and decline to base level on day 5. The migration of the cells into the intima begins on day 4, the intimal proliferation peaks on day 7 and declines to baseline around day 14. Having this information available, we considered it sufficient to validate our experimental conditions only at the time points of SSTR subset mRNA and protein determinations, i.e., before denudation and at 15 minutes, 3 days, 7 days and 14 days post denudation. Our results on the SMC proliferative and intimal responses were in complete agreement with the previously published results.

Here we find that all five SSTR mRNAs are expressed in rat aorta both as mRNA and protein. Importantly, the SSTR1,4 were clearly present both in the intimal and medial layers of the vascular wall. Aortic denudation induced a time-dependent subtype-selective response in pattern of SSTR expression. The earliest change occured in the case of SSTR1 and SSTR2 whose mRNA increased following denudation, reached peak levels between days 3–7 and declined to basal levels by day 14. SSTR3 and SSTR4 displayed a different pattern with a delayed, more gradual increase in mRNA beginning at day 3–7 and remaining elevated thereafter. SSTR5 was costitutively expressed with no change in level of expression during the 2 weeks post injury. By immunohistochemistry, SSTR antigens were localized predominantly in SMC that were present in the media or which had migrated into the intima. In general, the level of expression of SSTR1–5 by mRNA measurement correlated with receptor protein expression by immunohistochemistry.

Our results provide the first evidence for the expression of all five SSTRs in the aorta, and suggested that like other tissues, e.g., brain pituitary, and islet cells which also expressed the five SSTR isoforms, the aorta is an important target of SST action. Previously by RT-PCR, only SSTR2 mRNA was detected in rat iliac artery (Chen et al. 1997). By autoradiography, a rich concentration of SST binding sites has been described in peritumoral (but not normally) vessels, suggesting that SSTRs may be induced by a tumor product. We found a predominant cellular localization of SSTRs in SMC although lower levels of expression in endothelial or inflammatory cells cannot be ruled out. Functional SSTRs have also been identified in glomerular mesangial cells and in culturing intestinal SMC which express SSTRs with the pharmacological profile of the subtype 3 receptor.

What is the mechanism of SSTR induction by vascular injury? Steady state SSTR mRNA levels are augmented by cAMP, gastrin, EGF, and SST itself. Glucocorticoids acutely induce SSTR1 and SSTR2 mRNA whereas estrogen induces SSTR2 and SSTR3 mRNA and thyroid hormone upregulates SSTR1 and SSTR5 mRNA. The 5' upstream promoter regions of the four receptor genes that have been sequenced (SSTR1,2,4,5), display a number of consensus sequences that confer responsiveness to cAMP, AP1, AP2, Pit1, and thyroid hormone. The time course of increase in SSTR3 and SSTR4 mRNA in our study approximated the temporal profile of SMC hyperplasia suggesting that induction of these two subtypes may be a consequence of SMC replication. The earlier onset of induction of SSTR1 and SSTR2 suggests a difference mediator, possibly a growth factor such as EGF. Induction of endogenous SSTRs in response to vascular injury may represent a compensatory attempt to modulate the proliferative response by SST produced locally by inflammatory cells.

All five SSTRs are capable of inhibiting cell proliferation. SSTR1–4 act by stimulating PTP which dephosphorylates receptor tyrosine kinases thereby attenuating the mitogenic signal. SSTR5, on the other hand, inhibits guanylate cyclase and cGMP-dependent phosphorylation and activation of MAPK. Since the five SSTRs are expressed in the arterial wall, they could all be potential targets for the direct antiproliferative effects of SST. To date, however, only the effects of myointimale proliferation have been tested. Our findings suggest that SSTR1 or SSTR4 may be the optimal subtypes to target, given their appropriate localisation and time related induction during the proliferative stage in the vascular wall. In this respect, SSTR1 which is upregulated to a greater extent than SSTR2, and which is insensitive to the current generation of clinically used SST analogs, should be a prime candidate for further testing with SSTR1-selective compounds.

It will appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

REFERENCES

Asahara T, Bauters C, Pastore C, et al. Local delivery of vascular endothelial growth factor accelerates reendothelialization and attenuates intimal hyperplasia in balloon-injury rat carotid artery. Circulation 1995;91(2793–2801).

Bendeck MP, Irvin C, Reidy MA. Inhibition of Matrix Metalloproteinase Activity Inhibits Smooth Muscle Cell Migration but Not Neointimal Thickening After Injury. Circ Res 1996;78:38–43.

Bornfeldt KE, Raines EW, Graves LM et al. Platelet-derived growth factor-distinct signal transduction pathways associated with migration versus proliferation. N.Y. Acad Sci 1994.

Chen JC, Hsiang YN, Buchan AM. Somatostatin receptor expression in rat iliac arteries after balloon injury. J Invest Surg 1997;10(1–2):17–23.

Clowes A, Reidy M, Clowes M. Mechanism of stenosis after arterial injury. Lab Invest 1983;49(2):208–215.

Clowes A, Reidy M, Clowes M. Kinetics of cellular proliferation after arterial injury. Lab Invest 1983;49:327–333.

Clowes AW, Swartz SM. Significance of quiescent smooth muscle migration in the injured rat carotid artery. Circ Res 1985;56:139–45.

Emanuelsson H, Beatt KJ, Bagger JP, et al. Long-term effects of angiopeptin treatment in coronary angioplasty. Reduction of clinical events but not angiographic restenosis. European Angiopeptin Study Group [see comments]. Circulation 1995;91(6):1689–96.

Eriksen UH, Amtorp O, Bagger JP, et al. Randomized double-blind Scandinavian trial of angiopeptin versus placebo for the prevention of clinical events and restenosis after coronary balloon angioplasty. Am Heart J 1995;130(1):1–8.

von Essen R, Ostermaier R, Grube E, et al. Effects of octreotide treatment on restenosis after coronary angioplasty: results of the VERAS study. VErringerung der Restenoserate nach Angioplastie durch ein Somatostatin-analogon. Circulation 1997;96(5):1482–7.

Ferns GAA, Raines EW, Sprugel KH et al.. Inhibition of neointimal smooth muscle accumulation after angioplasty by an antibody to PDGF. Science 1991;253:1129–1132.

Foegh ML, Asotra S, Conte JV, et al. Early inhibition of myointimal proliferation by angiopeptin after balloon catheter injury in the rabbit. J Vasc Surg 1994;19(6):1084–91.

Foegh ML, Ramwell PW. Angiopeptin: experimental and clinical studies of inhibition of myointimal proliferation. Kidney Int Suppl 1995;52:S18–22.

Galis ZS, Muszynski M, Sukhova GK et al. Enhanced expression of vascular matrix metalloproteinases induced in vitro by cytokines and in regions of human atherosclerotic lesions. Ann NY Acad Sci 1995:501–507.

Goldberg I, Stemerman MB, Schnipper LE, Ransil BJ, Croocks GW, Fuhro RL. Vascular smooth muscle cell kinetics: a new assay for studying patterns of cellular proliferation in vivo. Science 1979;205:920–921.

Grant MB, Wargovich TJ, Ellis EA, Caballero S, Mansour M, Pepine CJ. Localisation of insulin-like growth factor I and inhibition of coronary smooth muscle cell growth by somatostatin analogues in human coronary smooth muscle cells. A potential tretment for restenosis? Circulation: 1994 1994;89:1511–1517.

Gronwald RG, Seifert RA, Bowen-Pope DF. Differential regulation of expression of two platelet-derived growth factor receptor subunits by transforming growth factor-beta. J Biol Chem 1989;264:8120–8125.

Hancock W, Adams DH, Wyner LR, Sayegh MH, Karnovsky MJ. CD4+mononuclear cells induce cytokine expression, vascular smooth muscle cell proliferation and arterial occlusion after endothelial injury. Am J Pat 1994;145:1008–1014.

Haudenschild CC, Swartz SM. Endothelial regeneration. Lab Invest 1979;41(5):407–418.

Holmes D, Vliestra R, Smith H, et al. Restenosis after percutaneous translumnal coronary angioplasty. Am J Cardiol 1984;53:77C–81C.

Holmes D, Holubkov R, Vliestra R, Registry AcotNTCA. Comparison of the complications during percutaneous transluminal angioplasty from 1977 to 1981 and from 1985 to 1986. J Am Coll Cardiol 1988 1988;22:1149–55.

Hong MK, Bhatti T, Matthews BJ, et al. The effect of porous infusion balloon-delivered angiopeptin on myointimal hyperplasia after balloon injury in the rabbit. Circulation (1993;88(2):638–48.

Häyry P, Isoniemi H, Yilmaz S, et al. Chronic allograft rejection. Immunol Rev 1993 Aug;134:33–81.

Häyry P, Myllärniemi M, Aavik E, et al. Stabile D-peptide analog of insulin-like growth factor-1 inhibits smooth muscle cell proliferation after carotid ballooning injury in the rat FASEB J 1995;9:1336–1344.

Häyry P, Raisanen A, Ustinov J, Mennander A, Paavonen T. Somatostatin analog lanreotide inhibits myocyte replication and several growth factors in allograft arteriosclerosis. FASEB J 1993;7(11):1055–60.

Lemström KB, Koskinen PK. Expression and localization of Platelet-Derived Growth Factor ligand and receptor protein during acute and chronic rejection of rat cardiac allografts. Circulation 1997;96:1240–1249.

Libby P, Galis Z. Cytokines regulate genes involved in atherosclerosis. Ann NY Acad Sci 1995;748:159–169, Lindner V, Reidy M. Proliferation of smooth muscle cells after vascular injury is inhibited by an antibody against basic fibroblast growth factor. Proc Natl Acad Sci 1991.

Majesky MW, Reidy MA, Bowen-Pope DF, Hart CE, Wilcox JN, Schwartz SM. PDGF ligand and receptor gene expression during repair of arterial injury. J Cell Biol 1990;111:2149–2158.

Majesky MW, M GC, Reidy MA, Schwartz S. Rat carotid neointimal smooth muscle cells reexpress developmentally regulated mRNA phenotype during repair of arterial injury. Circ Res 1992;71:759–768.

Myllärniemi M, Calderon L, Lemström K, Buchdunger E, Häyry P. Inhibition of platelet derived growth factor receptor tyrosine kinase inhibits vascular smooth muscle cell migration and proliferation. FASEB J 1997;11:1119–1126.

Nabel EG, Yang Z, Liptay S, et al. Recombinant platelet derived growth factor B gene expression in porcine arteries induced intimal hyperplasia in vivo. J Clin Invest 1993;91:1822–1829.

Patel YC. Molecular pharmacology of somatostatin receptor subtypes. J Endocrinol Invest 20;346–367, 1997.

Ross R. The pathogenesis of atherosclerosis: a perspective for the 1990s. Nature 1993;362(6423):801–9.

Shi Y, O'Brien JE, Fard A, Zalewski A. Transforming growth factor βI expression and myofibroblast formation during arterial repair. Arterioscler Thromb Vasc Biol 1996;16:1298–1305.

Sirois MG, Simons M, Edelman ER. Antisense oligonucleotide inhibition of PDGFR-β receptor subunit expression directs suppression of intimal thickening. Circulation 1997;95:669–676.

Tanaka H, Sukhova G, Schwartz D, Libby B. Proliferating arterial smooth muscle cells express TNF-α but not Interlukin-1 or Basic fibroblast growth factor. 1996.

Wrighton CJ, Hofer-Warbinek R, Moll T, Eytner R, Bach FH, de Martin R. Inhibition of Endothelial Cell Activation by Adenovirus-mediated Expression of IkBalfa, an Inhibitor of the Transcription Factor NF-KB. J Exp Med 1996;183:1–10.

Yumi K, Fagin JA, Yamashita M, et al. Direct effects of somatostatin analog octreotide on insulin-like growth factor-I in the arterial wall. Lab Invest. 1997;76(3):329–38.

---

What is claimed is:

1. A method for the prevention of a patient's fibroproliferative vasculopathy following vascular injury or a vascular surgical operation, said method comprising the administering to said patient an agonist specific for at least one somatostatin (SST) receptor showing an increased expression in the patients vascular wall subsequent to injury or operation, said administering being carried out for one to two weeks after the injury or surgical operation.

2. The method according to claim 1, wherein the fibroproliferative vasculopathy is selected from the group consisting of restenosis following coronary bypass surgery, PTCA (percutaneous transluminal coronary angioplasty), allograft arteriosclerosis in chromic allograft rejection, diabetic angiopathy and all forms of common arteriosclerosis.

3. The method according to claim 2 wherein the fibroproliferative vasculopathy is vascular restenosis.

4. The method according to claim 3 wherein the surgical operation is balloon angioplasty or a coronary bypass operation.

5. The method according to claim 2 wherein the fibroproliferative vasculopathy is chronic allograft rejection.

6. The method according to claim 1 wherein said SST-receptor shows an increased expression during the first week following the injury or the surgical operation.

7. The method according to claim 6 wherein the SST-receptor is the SST-receptor subtype 1 or subtype 4.

8. The method according to claim 1 wherein the administering of the receptor agonist is started a few days before the surgical operation.

9. The method according to claim 1 wherein the receptor agonist is a compound selected from the group consisting of somatostatin SRIF-14, somatostatin SRIF-28 and DADI-SST14.

10. The method according to claim 1 wherein the agonist is somatostatin SRIF-14.

* * * * *